United States Patent [19]

Light et al.

[11] 4,064,184

[45] Dec. 20, 1977

[54] NORBORNANOL DERIVATIVES

[75] Inventors: Kenneth K. Light, Long Branch; Manfred Hugo Vock, Locust, both of N.J.; Edward J. Shuster, Brooklyn, N.Y.; Frederick Louis Schmitt, Holmdel, N.J.

[73] Assignee: International Flavors & Fragrances Inc., New York, N.Y.

[21] Appl. No.: 740,937

[22] Filed: Nov. 11, 1976

[51] Int. Cl.² .............................................. C07C 35/21
[52] U.S. Cl. ............................... 260/617 R; 252/132; 252/173; 252/522; 252/557; 424/49; 426/538; 426/650
[58] Field of Search .................................. 260/617 R

[56] References Cited
U.S. PATENT DOCUMENTS 3,879,466  11/1975  Light ............................. 260/617 R Primary Examiner—Norman Morgenstern
Attorney, Agent, or Firm—Arthur L. Liberman; Franklin D. Wolffe

[57] ABSTRACT

Processes and compositions are described for the use in foodstuff, chewing gum, toothpaste and medicinal product flavor and aroma and perfume aroma augmenting, enhancing, modifying and imparting compositions and as foodstuff, chewing gum, toothpaste, medicinal product, perfume and perfumed article aroma imparting materials of 3,3-dimethyl-2(3-butenyl) norbornanol-2 (hereinafter referred to as the "norbornanol derivative" having the structure:

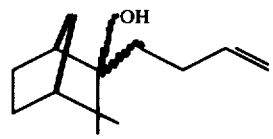

(which structure is intended to cover both the "endo" and the "exo" isomers thereof) produced by a process which comprises reacting an allylic Grignard reagent having the structure:

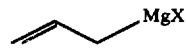

wherein X is chloro, bromo or iodo with camphene oxide having the structure:

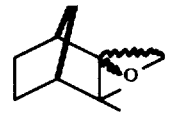

by either "exo" camphene oxide or "endo" camphene oxide or a mixture of "exo" and "endo" camphene oxide. Addition of the said norbornanol derivative to consumable materials is indicated to produce:

a. In foodstuffs, foodstuff flavorings, chewing gums, toothpastes and medicinal products, sweet, fruity, berry-like aromas with woody, incense-like, cedarwood-like, tea-like and floral nuances and incense-like and cedarwood-like flavors with rosey, berry and tea-like nuances; and b. In perfumes, colognes and perfumed articles, sweet, woody, thujone-like aromas with strong fir-balsam, armoise, cedarleaf, piney, earthy and camphoraceous nuances.

6 Claims, 2 Drawing Figures

NMR SPECTRUM FOR EXAMPLE I
SOLVENT: CDCL₃
SWEEP WIDTH: 1000 CPS.

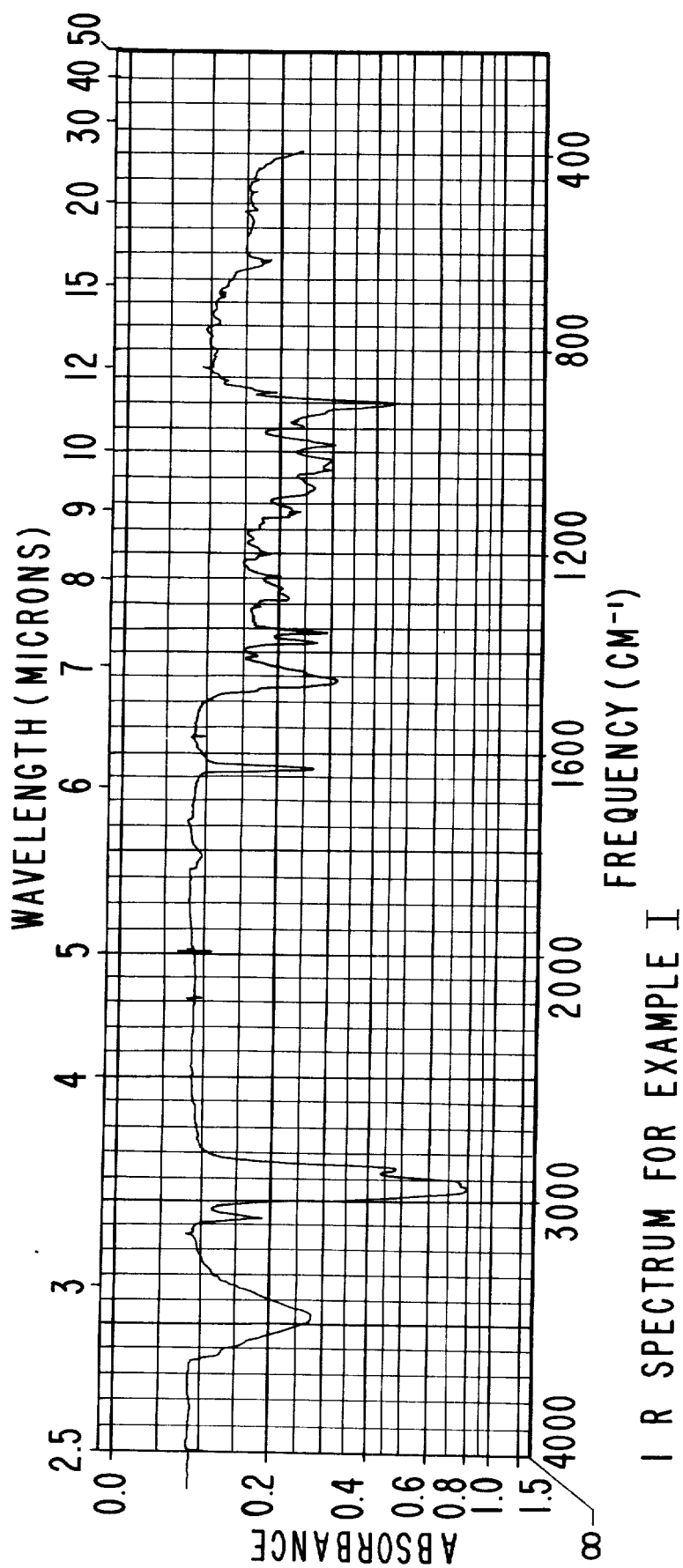

NORBORNANOL DERIVATIVES

BACKGROUND OF THE INVENTION

The present invention relates to the 3,3-dimethyl-2(3-butenyl) norbornanol-2 produced by the novel processes of our invention, and novel compositions using said norbornanol derivative to augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply and to provide more uniform properties in the finished product.

Sweet, fruity, berry-like aromas with woody, incense-like, cedarwood-like, tea-like and floral nuances and incense-like and cedarwood-like flavors with rosey, berry and tea-like nuances are particularly desirable for many uses in foodstuff flavors, chewing gum flavors, toothpaste flavors and medicinal product flavors.

Sweet, woody, thujone-like aromas with strong fir-balsam, armoise, cedarleaf, piney, earthy and camphoraceous nuances are desirable in several types of perfume compositions, perfumed articles and colognes.

U.S. Pat. No. 3,852,358 issued on Dec. 3, 1974 discloses a process for producing 2-acetyl-3,3-dimethyl-5-norbornene in both the exo and endo forms which have uses in perfumery and other fragrance applications. These compounds have the structures:

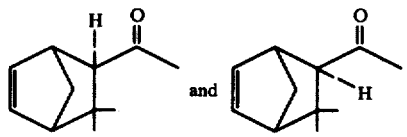

These compounds, produced by reaction of cyclopentadiene with mesityl oxide, are starting materials for producing a number of the compounds of our invention. However, the compounds of our inventin have unexpected, unobvious and advantageous properties when compared with the 2-acetyl-3,3-dimethyl-5-norbornene of U.S. Pat. No. 3,852,358.

U.S. Pat. No. 3,942,761 discloses the use in perfumery of 4(2'-norbornyl)-2-butanones having the structure:

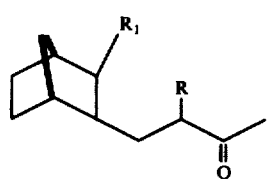

wherein R₁ is hydrogen or methyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

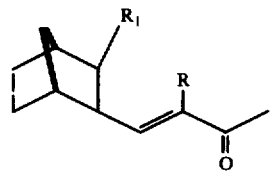

wherein the dotted line is a carbon-carbon single bond or a carbon-carbon double bond. In addition, the following reaction sequence is set forth therein:

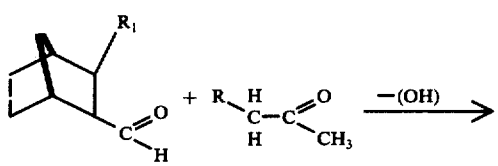

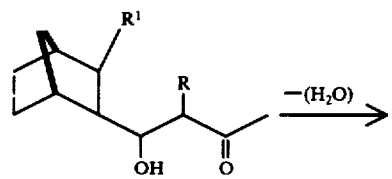

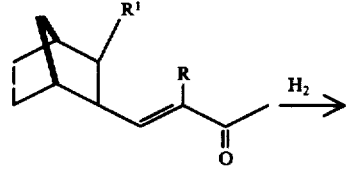

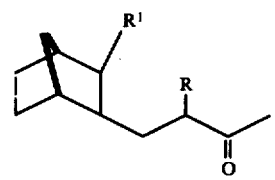

Arctander, "Perfume and Flavor Chemicals", 1969, Vol. 1, discloses the use in perfume compositions and in foodstuff flavors of "fenchone", "fenchyl alcohol", "camphene carbinol", and "camphene carbinyl acetate", thus:

i. "1358: FENCHONE
  laevo-Fenchone. (dextro- is known but less common as a fragrance material).
  1,3,3-Trimethyl-2-norbornanone.
  1,3,3-Trimethyl bicyclo-1,2,2-heptanone-2.

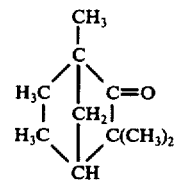

Warm-camphoraceous, powerful and diffusive, basically sweet odor.

Warm, somewhat burning and bitter taste with a medicinal note.

This ketone finds some use as a masking odor in industrial fragrances. It is also used in the reconstruction of Fennel oil and a few other essential oils.

In spite of its rather unpleasant taste, it is used in various Berry complex flavors, in Spice complexes and in certain types of Liquer flavoring.

The concentration used in about 0.1 to 5 ppm in the finished product".

ii. "1387: FENCHYL ALCOHOL
1,3,3-Trimethyl-2-norbornanol.
1,3,3-Trimethyl bicyclo-1,2,2-heptanol-2.
2-Fenchanol.
Fenchol.

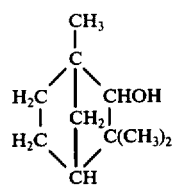

The racemic alpha-Fenchol has a somewhat lower melting point, and the beta-Fenchols are all liquid at room temperature.

Fenchol made by reduction of Fenchone from Cedar-leaf oil is usually a mixture of several isomers, including the crystalline alpha-isomers. The beta-isomer forms a crystalline Hydrate which may be solid at room temperature.

Almost insoluble in water, soluble in alcohol, miscible with oils. Powerful and diffusive, Camphor-like, but sweeter and more Citrus-like almost Lime-like odor with more or less of an earthy-dry character, according to the composition and isomer-ratio.

The taste is somewhat bitter-Lime-like, camphoraceous and slightly woody-musty.

This interesting alcohol (or mixed alcohols) finds use in perfume compositions ranging from woody or herbaceous to Citrus-Lime and even certain floral types. It produces power and "lift" to floral fragrances, and solid background to Lime and other Citrus bases, having the advantage over the Terpenes in being very stable in soap.

Fenchyl alcohol is also used in flavor compositions such as Strawberry and other berries, Lime and Spice, etc.

The concentratin is normally low, e.g. 0.2 up to 5 ppm in the finished product".

iii. "1028: 3,3-DIMETHYL-Δ², beta-NORBORNANE-2-ETHANOL "Camphene carbinol".

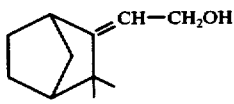

Sweet-camphoraceous, warm and soft odor with a woody undertone. Upon standing it may develop on odor resembling that of Celluloid.

Although rarely offered commercially, this chemical could find some use in perfume compositions of the woody, Oriental and orrisy type, in new variations of Pine fragrances, and in various soap and detergent perfumes".

iv. "1029: 3,3-DIMETHYL-Δ²-beta-NORBORNANE-2-ETHYLACETATE "Camphene carbonyl acetate".

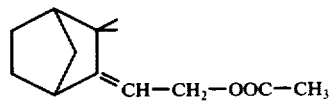

Mild and sweet-woody odor with a floral-piney undertone. The commercial products are probably not well-defined single chemicals, and great variations in odor have been observed.

This ester has been developed in line with the research on Sandalwood type odors. The parent alcohol "Camphene carbinol" was once considered useful as a Sandlewood type material, but it has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso-Bornylacetate, Nitromusks, etc.".

U.S. Pat. No. 3,928,456 discloses monocyclic compounds having the generic structure:

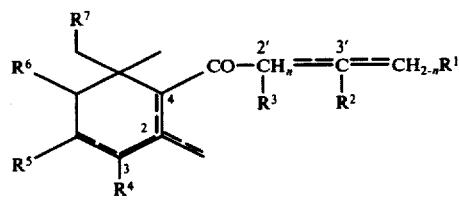

containing one double bond in positon 2'- or 3'- of the acyl side-chain and either one double bond in position 1- or 2-(as shown in the above formula, the double bond in the 2 position can be either in the cycle or the side chain), or two conjugated double bonds in positions 1- or 3- of the cycle, the double bonds being represented by dotted lines, and wherein $n$ is zero or 1, $R^1$, $R^2$ and $R^3$ represent hydrogen or one of them a lower alkyl radical, such as methyl or ethyl, and the others hydrogen, and $R^4$, $R^5$, $R^6$ and $R^7$ represent hydrogen or one of them a lower alkyl radical, such as methyl or ethyl, and the others hydrogen, as being useful in perfumery and food flavors and also flavors, beverages, animal feeds and tobaccos. Specifically disclosed in this patent is a compound having the structure:

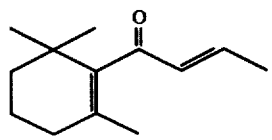

U.S. Application for Letters Patent Ser. No. 551,030, filed on Feb. 19, 1975 discloses, interalia, perfumery users of coumpounds having the structures:

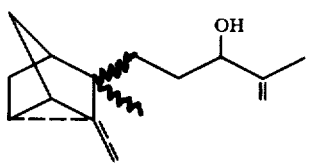

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line.

In addition, various processes and compounds relating to the synthesis of synthetic sandalwood oil components are described in the following U.S. Patents:

i. Perfume Compounds And Process For Preparing Same 3,673,261 issued June 27, 1972:
Compounds:

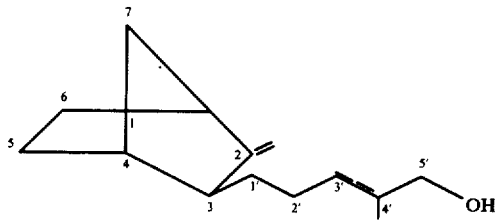

2-methylene-3-exo(trans-4'-methyl-5'-hydroxypent-3'-enyl)bicyclo[2.2.1]-heptane    trans-3-Normethyl-beta-santalol

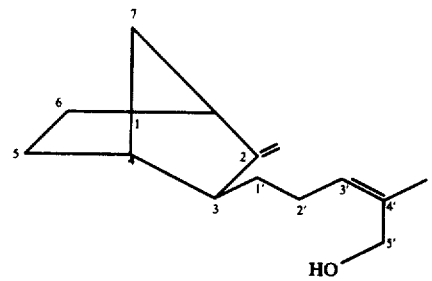

2-methylene-3-exo(cis-4'-methyl-5'-hydroxypent-3'-enyl)bicyclo[2.2.1]-heptane    cis-3-normethyl-beta-santalol

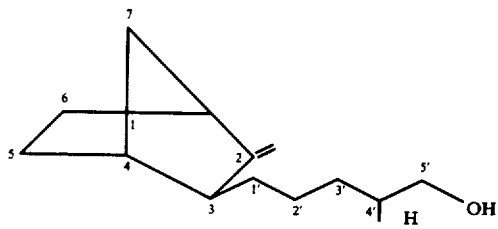

2-methylene-3-exo(4'-methyl-5'-hydroxypentyl)bicyclo[2.2.1]heptane-3-normethyldihydro-beta-santalol ii. Dihydro-beta-santalol and Processes For Preparing Dihydro-beta-Santalol From 3-Endo-Methyl-3-Exo(4'-Methyl-5'-Hydroxyphenyl) Norcamphor - U.S. Pat. No. 3,673,263 issued June 27, 1972:

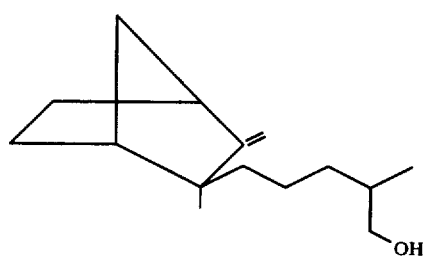

dihydro-beta-santalol iii. Process for Preparing Beta-Santalol From 3-Methylnorcamphor - U.S. Pat. No. 3,662,008 issued May 9, 1972:

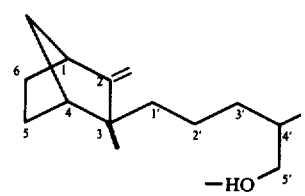

endo-3-methyl-exo-3(cis-5'-hydroxy-4'-methylpent-3'-enyl)-2-methylenebicyclo-(2.2.1) heptane

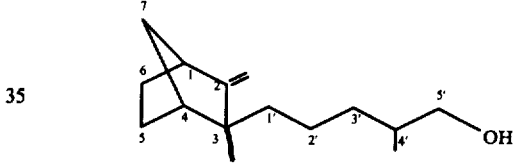

endo-3-methyl-exo-3(trans-5'-hydroxy-4'-methylpent-3'-enyl)-2-methylenebicyclo(2.2.1) heptane iv. Process For Preparing Dihydro-Beta-Santalol From 3-Endo-Methyl-3-Exo(4'-methyl-5'-Hydroxypentyl) Norcamphor - U.S. Pat. No. 3,673,266, issued June 27, 1972:

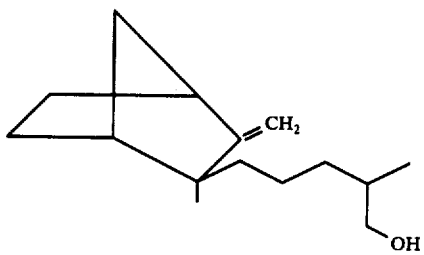

dihydro-beta-santalol

None of the compounds disclosed in either U.S. Pat. No. 3,928,456 or U.S. application for Letters Patent Ser. No. 551,030, filed Feb. 19, 1975 have properties even closely similar to the properties of the norbornanol derivative of the instant application.

Chem. Abstracts, Vol. 84, 73728n (abstract of Karaev, et al, Zh.Org.Khim. 1975, 11(12), 2622) discloses preparation of the compound:

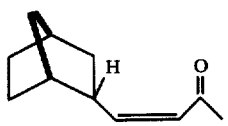

by reaction of:

with

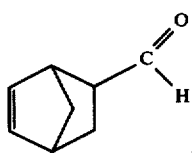

to form:

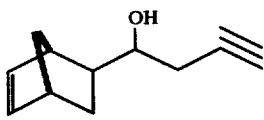

followed by isomerization with HgO/H₂SO₄.

Klein and Rojahn, Chem.Abstracts, Vol. 84, 90327y (1976) discloses the use of compounds having the generic structure:

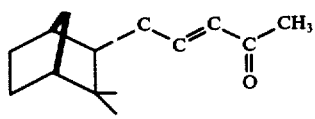

(wherein the dashed line is a single or double bond) as an intermediate in the preparation of beta-santalol; but no organoleptic properties of these norbornane derivatives are disclosed.

U.S. Pat. No. 3,748,344, issued on July 24, 1973, discloses that chemical compounds characterized by the structural formula:

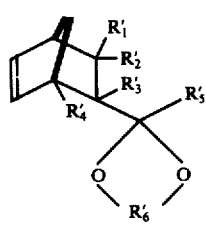

wherein the dashed line represents the presence of a single or a double bond wherein $R_1'$, $R_2'$, $R_3'$, and $R_4'$ each represent hydrogen or lower methyl and $R_5'$ represents hydrogen or lower alkyl and $R_6'$ represents a polymethylene radical of from 2 to 4 carbon atoms which is unsubstituted or substituted with lower alkyl, which "as a whole exhibits a characteristic, pleasant, strong and long lasting aroma which is highly useful in the preparation of fragrance compositions and perfume products". Various notes are described such as green, cuminic, walnut, raw potato, earthy, camphoraceous, civet, walnut bark, neroli, anise, vegetable, menthone, animal, minty eucalyptol, cucumber, pine and fecal.

In addition, U.S. Pat. No. 3,748,344 discloses as chemical intermediates for preparing the above ketal, a compound having the generic structure:

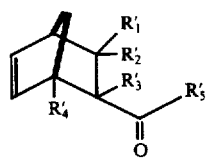

wherein $R_1'$, $R_2'$, $R_3'$, $R_4'$, and $R_5'$ have the same meaning as defind above.

However, the specific compound of our invention is not set forth in U.S. Pat. No. 3,748,344.

No prediction of the oganoleptic properties of the compound of the instant invention can be made by a study of the disclosure of U.S. Pat. No. 3,748,344.

Chemical Abstracts, Vol. 71, 49664z (abstract of SadykhZade, et al (U.S.S.R.) Dokl. Akad. Nauk Azerb. SSR 1968, 24(11), 38-41) discloses the synthesis of exo and endo forms of the compounds having the structures:

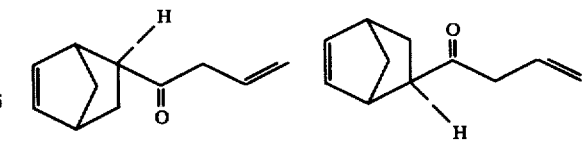

Chemical Abstracts, Vol. 81, 135512m (abstract of Akhmedov, I.M., et al (Inst. Georg. Fiz. Khim., Baku, U.S.S.R.). Dokl. Akad, Nauk Az. SSR 1974, 30(4), 18-21) discloses the synthesis of the compound having the structure:

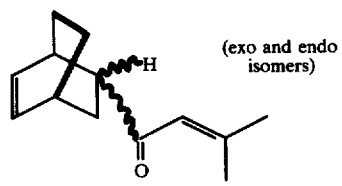

(exo and endo isomers)

None of the Chemical Abstracts references discloses compounds which have a close structural relationship to the compound of the instant invention. In any event, the organoleptic properties of the compounds of the Chemical Abstract references are different in kind from those of the compound of the instant invention.

BRIEF DESCRIPTION OF THE DRAWINGS

FIG. 2 is the Infrared spectrum for the norbornanol derivative of our invention produced in Example I.

THE INVENTION

Figure 1:
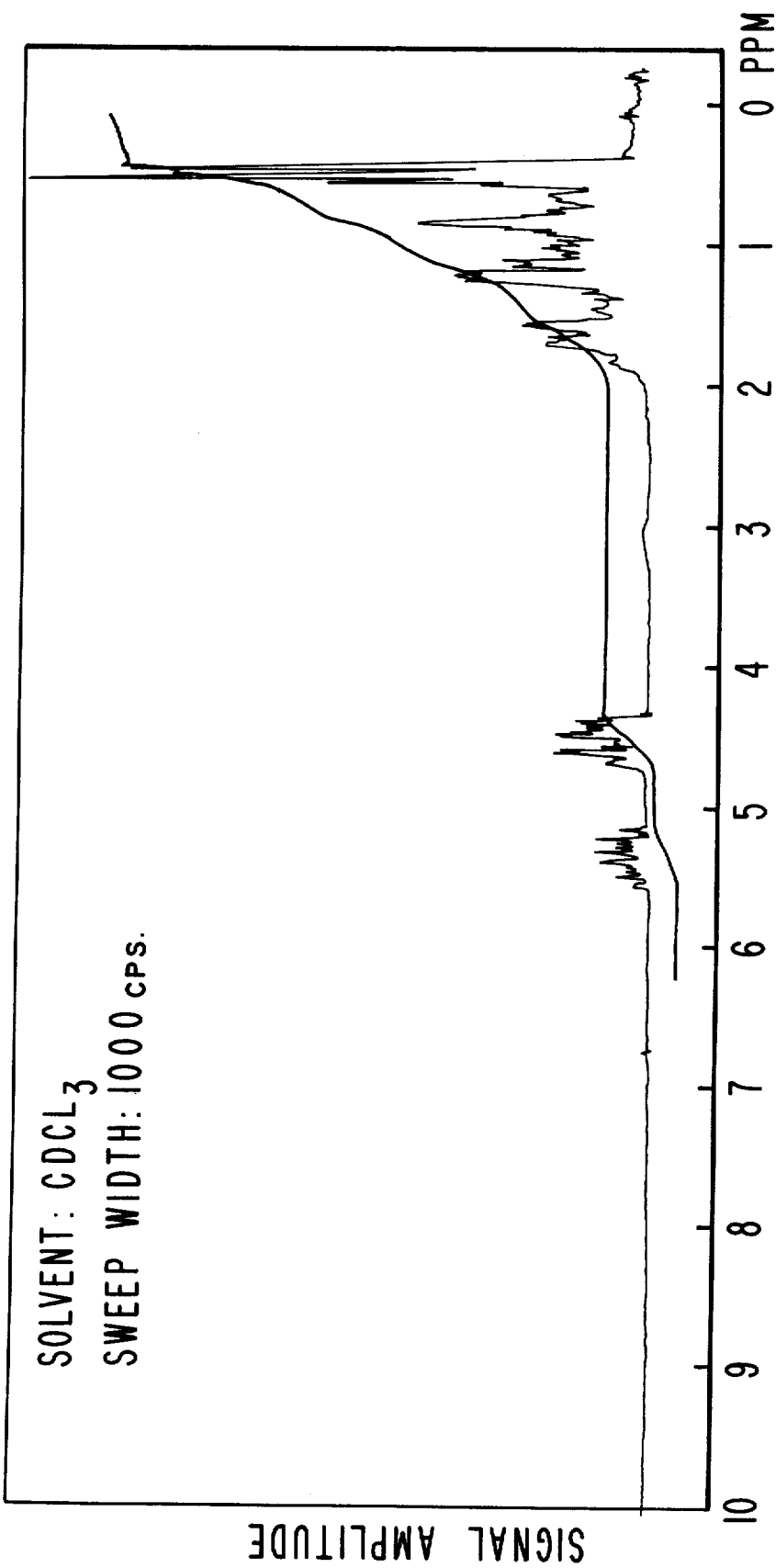
FIG. 1 is the NMR spectrum for the norbornanol derivative of our invention produced in Example I.

It has now been discovered that novel solid and liquid foodstuff, chewing gum, medicinal product and toothpaste compositions and flavoring compositions therefor having sweet, fruity, berry-like aromas with woody, incense-like, cedarwood-like, tea-like and floral nuances and incense-like and cedarwood-like flavors with rosey, berry and tea-like nuances and novel perfume compositions, colognes and perfumed articles having sweet, woody, thujonelike aromas with strong fir-balsam, armoise, cedarleaf, piney, earthy and camphoraceous nuances, may be provided by the utilization of the compound 3,3-dimethyl-2(3-butenyl)norbornanol-2 having the structure:

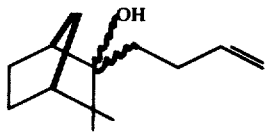

as the "endo", "exo" form or mixture of "endo" and "exo" forms.

The 3,3-dimethyl-2(3-butenyl) norbornanol-2 useful as indicated supra may be produced by the process of admixing a Grignard reagent having the structure:

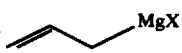

wherein X is chloro, bromo or iodo with camphene oxide having the structure:

(either the "endo", "exo" or mixture of "endo" or "exo" forms), thereby forming an organo metallic salt, which is then hydrolyzed using acid. The reaction sequence is as follows:

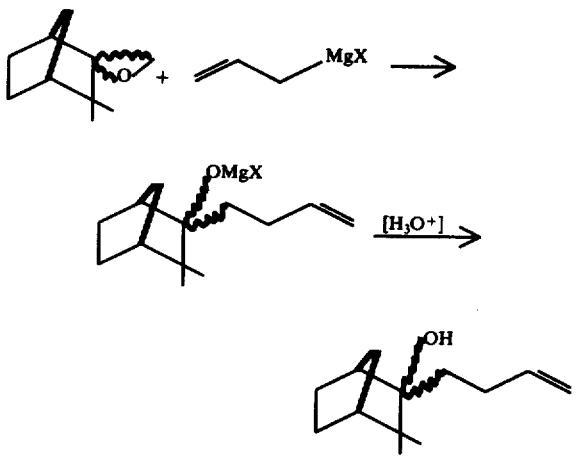

The reaction with the allylic Grignard reagent takes place at a temperature of between 25° and 50° C in the presence of a solvent inert to any of the reactants, diethyl ether or tetrahydrofuran. The Grignard reagent is first formed in the presence of the same solvent by reacting magnesium with an allylic halide; allyl chloride, allyl bromide or allyl iodide, then camphene oxide is previously pre-mixed with additional allyl chloride and the resulting mixture is added into the pre-formed Grignard reagent. The reaction time in forming the organometallic salt, at a temperature of 40° C, is between 2 and 10 hours. At higher temperatures the reaction time is somewhat shorter.

The hydrogenation of the organometallic salt to the tertiary alcohol orbornanol derivative of our invention takes place at a temperature in the range of between 20°-60° C using a mineral acid such as hydrochloric acid, sulfuric acid, phosphoric acid or paratoluene sulfonic acid. The reaction takes place in an excess of water, which is one of the reactants.

At the end of the reaction, the reaction mass is concentrated and the desired product is fractionally distilled at a low pressure (of between 1 and 10 mm Hg).

When the norbornanol derivative of our invention is used as a food flavor adjuvant, the nature of the coingredients included with said norbornanol derivative in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to means the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the norbornanol derivative of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascrobate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentonic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1,cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl buryrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1,-diethoxy-ethane, 1,1-dimethoxyethane and dimethoxymethane).

The specific flavoring adjuvant selected for use may be either solid or liquid depending upon the desired physical form of the ultimate product, i.e, foodstuff, whether simulated or natural, and should, in any event, (i) be organoleptically compatible with the norbornanol derivative of our invention by not covering or spoiling the organoleptic properties (aroma and/or taste) thereof; (ii) be nonreactive with the norbornanol derivative of our invention and (iii) be capable of providing an environment in which the norbornanol derivative can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of norbornanol derivative employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of norbornanol derivative will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of norbornanol derivative ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the norbornanol derivative is added to the foodstuff as an integral component of a flavoring composition, it is, of course, essential that the total quantity of flavoring composition employed be sufficient to yield an effective norbornanol derivative concentration in the foodstuff product.

Food flavoring compositions prepared in accordance with the present invention preferably contain the norbornanol derivative in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornanol derivative with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the norbornanol derivative in a dry blender until the requisite degree of uniformity is achieved.

It is presently preferred to combine with the norbornanol derivative of our invention, the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrizine;
2-Ethyl-3-methyl pyrizine;
3-Phenyl-4-pentenal
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene);
Beta-cyclohomocitral (2,2,6-trimethylcyclohex-1-ene carboxaldehyde);
Isoamyl butyrate;
Cis-3-hexanol-1;
2-Methyl-2-pentenoic acid;
Elemecine (4-allyl-1,2,6-trimethoxy benzene;
Isoelemecine (4-propenyl-1,2,6-trimethoxy benzene; and
2-(4-Hydroxy-4-methylpentyl) norbornadiene prepared according to U.S. application for Letters Patent Ser. No. 461,703, filed on Apr. 17, 1974

The norbornanol derivative and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably in woody and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the norbornanol derivative of our invention can be used to alter, modify or enhance the aroma characteristics of a perfume composition, for example, by utilizing or moderating the olfactory reaction contributed by another ingredient in the composition.

The amount of norbornanol derivative of our invention which will be effective in perfume compositions as well as in perfumed articles and colognes depends on many factors, including the other ingredients, their amounts and the effects which are desired. It has been found that perfume compositions containing as little as 0.01% or norbornanol derivative or even less (e.g., 0.005%) can be used to impart a sweet, woody, thujone-like aroma with strong fir-balsam, armoise, cedarleaf, piney, earthy an camphoraceous nuances to soaps, cosmetics or other products. The amount employed can range up to 70% of the fragrance components and will depend on considerations of cost, nature of the end product, the effect desired on the finished product and the particular fragrance sought.

The norbornanol derivative of our invention is useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of the norbornanol derivative of our invention will suffice to impart an intense thujone-like note to woody and/or piney formulations. Generally, no more than 3% of the norbornanol derivative of our invention, based on the ultimate end product, is required in the perfume composition.

In addition, the perfume composition or fragrance composition of our invention can contain a vehicle, or carried for the norbornanol derivative. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the norbornanol derivative of our invention can be utilized to alter, modify or enhance sensory properties, particularly organoleptic properties, such as flavor(s) and/or fragrance(s) of a wide variety of consumable materials.

The following Examples serve to illustrate our invention and this invention is to be considered restricted thereto only as indicated in the appended claims.

All parts and percentages given herein are by weight unless otherwise specified.

EXAMPLE I

Production of 3,3-Dimethyl-2(3-Butenyl) Norbornanol-2

Reaction:

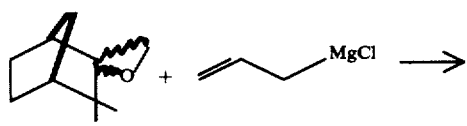

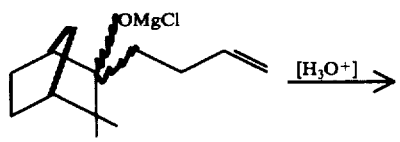

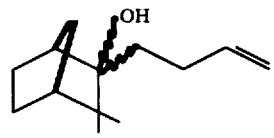

Into a 12 liter reaction vessel is placed 164 grams of magnesium and 985 grams of tetrahydrofuran. While stirring the magnesium/tetrahydrofuran mixture, 20 grams of allyl chloride is added and the temperature of the reaction mass rises to 40° C. A mixture of 2410 grams of camphene oxide (43% in benzene solution) and 520 grams of allyl chloride is slowly added to the reaction mass and the reaction mass is maintained at a temperature of 35°-40° C with external cooling. The allyl chloride and camphene oxide are added over a period of 7 hours. 10 Grams of additional magnesium is added and stirring is continued for an extra hour while maintaining the reaction mass at 40° C with external cooling. The reaction mass is then cooled to room temperature and maintained at room temperature for a period of 15 hours.

6.8 Liters of water is then admixed with 170 grams of concentrated 93% sulfuric acid. The 3.8 liters of reaction product is then added to the sulfuric acid solution whereupon the temperature rises from 20° up to 40° C. The resulting mixture is an emulsion and, in order to separate the phases of the emulsion, a solution containing 178 grams of concentrated sulfuric acid and 1200 ml water is added. The water and the organic layers are separated and the organic layer is washed with 1 liter of water containing 5 grams of concentrated sulfuric acid solution by two 100 ml portions of water. The organic layer is then stripped on a Rotovap yielding 1249 grams of product, which is then fractionally distilled on an 8 inch Goodloe column after adding thereto 41 grams of Primol ®. The following fractions are produced:

| Fraction # | Vapor Temperature (° C) | Liquid Temperature (° C) | Vacuum mm Hg | Weight (g) |
|---|---|---|---|---|
| 1 | 43–60 | 124–122 | 3 | — |
| 2 | 60 | 111 | 2 | — |
| 3 | 65 | 108 | 1 | — |
| 4 | 76 | 115 | 1 | — |
| 5 | 80 | 118 | 1 | — |
| 6 | 91 | 122 | 1 | — |
| 7 | 91 | 121 | 1 | 18.9 |
| 8 | 90–95 | 128–126 | 3 | 3.7 |
| 9 | 101 | 123 | 3 | 26.4 |
| 10 | 103 | 123 | 3 | 28.3 |
| 11 | 103 | 123 | 3 | 37.8 |
| 12 | 101 | 124 | 3 | 23.4 |
| 13 | 86 | 124 | 1 | 41.5 |
| 14 | 88 | 124 | 1 | 38.4 |
| 15 | 88 | 124 | 1 | 31.6 |
| 16 | 91 | 125 | 1 | 36 |
| 17 | 93 | 126 | 1.5 | 76.5 |
| 18 | 86 | 122 | 1 | 81.3 |
| 19 | 102 | 125 | 2 | 59.3 |
| 20 | 88 | 125 | 2 | 75.9 |
| 21 | 88 | 125 | 2 | 64.1 |
| 22 | 88 | 127 | 2 | 60.3 |
| 23 | 88 | 134 | 2 | 44.5 |
| 24 | 93 | 161 | 2 | 40.1 |
| 25 | 91 | 196 | 2 | 40.2 |

Fractions 12–23 are substantially all product and are combined yielding 633 grams of good material.

| The NMR analysis is as follows: | |
|---|---|
| δ, ppm | Interpretation |
| 0.89 | (s, 3H) |

-continued

| The NMR analysis is as follows: δ, ppm | Interpretation |
|---|---|
| 0.95 | (s, 3H) |
| 0.95–2.5 | (m, 12H) |
| 4.85 | (m, 2H) |
| 5.85 | (m, 1H) |

The Mass Spectral analysis is as follows:
m/e = 55, 41, 111, 69, 43

FIG. 1 sets forth the NMR spectrum for the resulting product. FIG. 2 sets forth the Infrared spectrum for the resulting product.

EXAMPLE II

Flavor Formulation Using the Material Produced in Example I

The following basic cinnamon flavor is formulated:

| Ingredient | Parts by Weight |
|---|---|
| Cinnamic Aldehyde | 70 |
| Eugenol | 15 |
| Cuminic Aldehyde | 1.0 |
| Furfural | 0.5 |
| Methyl Cinnamate | 5.0 |
| Cassia Oil | 8.5 |
| | 100.0 TOTAL |

Fraction 5 is incorporated at the rate of 5% into the above-mentioned flavor formulation, and so incorporated, adds a more cinnamon bark-like character in aroma and taste and a more woody, sweet aroma. It is preferred over the same formulation not containing the 3,3-dimethyl-2(3-butenyl) norbornanol-2.

EXAMPLE III

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 3,3-dimethyl-2(3-butenyl) norbornanol-2 produced according to Example I | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptyl cyclopentanone | 5 |
| | 353.3 (TOTAL) |

The foregoing blend is evaluated and found to have a high degree of richness and persistence in its novel natural piney quality. This base composition can be admixed with aqueous ethanol, chilled and filtered to produce a finished cologne. The cologne so prepared has a sweet, woody, thujone-like aroma with strong fir-balsam, armoise, cedarleaf, piney, earthy and camphoraceous nuances. The base composition can also be used to scent soap or other toilet goods such as lotions, aerosols, sprays and the like.

EXAMPLE IV

Preparation of a Cosmetic-Powder Composition

A cosmetic powder is prepared by mixing in a ball mill, 100 g of talcum powder with 0.25 g of 3,3-diemthyl-2(3-butenyl) norbornanol-2 prepared according to Example I. It has an excellent sweet, woody, thujone-like aroma.

EXAMPLE V

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with a sweet, woody, thujone-like aroma are prepared containing 0.10%, 0.15% and 0.20% of 3,3-dimethyl-2(3-butenyl) norbornanol-2 prepared according to Example I. They are prepared by adding and homogeneously mixing the appropriate quantity of 3,3-dimethyl-2(3-butenyl) norbornanol-2 in the liquid detergent. The detergents all possess a sweet, woody thujone-like fragrance, the intensity increasing with greater concentrations of 3,3-dimethyl-2(3-butenyl) norbornanol-2.

EXAMPLE VI

Preparation of a Cologne and Handkerchief Perfume 3,3-Dimethyl-2(3-butenyl) norbornanol-2 prepared according to the process of Example I is incorporated in a cologne at a concentration of 2.5% in 85% aqueous ethanol; and into a handkerchief perfume at a concentration of 20% (in 95% aqueous ethanol). A distinct and definite sweet, woody, thujone-like fragrance is imparted to the cologne and to the handkerchief perfume.

EXAMPLE VII

Preparation of a Cologne and Handkerchief Perfume

The composition of Example I is incorporated in a cologne at a concentration of 2.5% in 85% aqueous ethanol; and into a handkerchief perfume at a concentration of 20% (in 95% aqueous ethanol). The use of 3,3-dimethyl-2(3-butenyl) norbornanol-2 in the composition of Example I affords a distinct and definite sweet, woody, thujone-like aroma with strong, fir-balsam, armoise, cedarleaf, piney, earthy and camphoraceous notes to the handkerchief perfume and cologne.

EXAMPLE VIII

Preparation of Soap Composition

One hundred grams of soap chips are mixed with one gram of 3,3-dimethyl-2(3-butenyl) norbornanol-2 of Example I until a substantially homogeneous composition is obtained. The perfumed soap composition manifests an excellent sweet, woody, thujone-like aroma.

EXAMPLE IX

Preparation of a Detergent Composition

A total of 100 g of a detergent powder (Lysine salt of n-dodecyl benzene sulfonic acid as more specifically described in U.S. Pat. No. 3,948,818, issued on Apr. 6, 1976) is mixed with 0.15 g of the 3,3-dimethyl-2(3-butenyl) norbornanol-2 of Example I until a substantially homogeneous composition is obtained. This composition has an excellent sweet, woody, thujone-like aroma.

EXAMPLE X 3,3-Dimethyl-2(3-butenyl) norbornanol-2 is shown to be of advantage when compounded into the following herbal formulation at a concentration of 15% by weight:

| Ingredient | Parts by Weight |
|---|---|
| Oakmoss absolute 50% in diethyl phthalate | 20 |
| alpha-methyl-3,4-methylene-dioxy hydrocinnamic aldehyde | 10 |
| Methyl Dihydro Jasmonate | 100 |
| Coumarin | 20 |
| Musk Ketone | 80 |
| Isocyclocitral (10% in diethyl phthalate) | 10 |
| Galbanum Oil (10% in diethyl phthalate) | 6 |
| Rosemary Oil | 10 |
| Pine Needle Oil | 60 |
| Fir Balsam Absolute (10% in diethyl phthalate) | 10 |
| Bergamot Oil | 60 |
| Benzyl Acetate | 320 |
| Linalool | 80 |
| Indol (10% in diethyl phthalate) | 6 |
| Undecalactone (10% in diethyl phthalate) | 12 |
| Ylang Ylang Oil | 32 |
| Lemon Oil | 14 |
| 3,3-Dimethyl-2(3-butenyl) norbornanol-2 produced according to Example I | 150 |
| Total | 1000 |

The addition of 15% of 3,3-dimethyl-2(3-butenyl) norbornanol-2 to the above formulation contributes a rich woody thujone-like nuance to the fragrance. The character of the perfume is substantially improved by this addition. The addition tends to round out the fragrance, rendering it more complete.

This 3,3-dimethyl-2(3-butenyl) norbornanol-2 may be used effectively in many types of formulations at concentrations ranging from 10% up to 50%. Higher concentrations may be used to create special effects.

What is claimed is:

1. The compound having the structure:

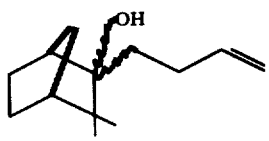

wherein the wavy lines are representative of "exo" or "endo" configurations.

2. The compound of claim 1 having the structure:

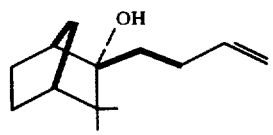

3. The compound of claim 1 having the structure:

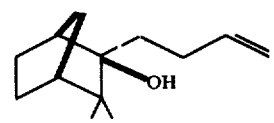

4. The compound having the structure:

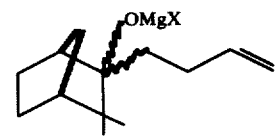

wherein each of the wavy lines represents an "exo" or "endo" configuration and X is selected from the group consisting of chlorine, bromine or iodine.

5. The compound of claim 4 having the structure:

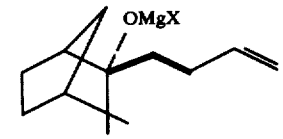

6. The compound of claim 4 having the structure:

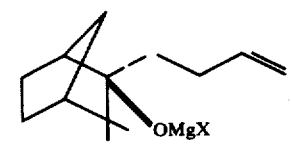

* * * * *